(12) United States Patent
Willbold

(10) Patent No.: US 11,274,125 B2
(45) Date of Patent: *Mar. 15, 2022

(54) AMYLOID-BETA-BINDING PEPTIDES AND THE USE THEREOF FOR THE TREATMENT AND DIAGNOSIS OF ALZHEIMER'S DISEASE

(71) Applicant: FORSCHUNGSZENTRUM JUELICH GMBH, Juelich (DE)

(72) Inventor: Dieter Willbold, Juelich (DE)

(73) Assignee: PRIAVOID GMBH, Juelich (DE)

( * ) Notice: Subject to any disclaimer, the term of this patent is extended or adjusted under 35 U.S.C. 154(b) by 24 days.

This patent is subject to a terminal disclaimer.

(21) Appl. No.: 16/908,606

(22) Filed: Jun. 22, 2020

(65) Prior Publication Data

US 2020/0317734 A1 Oct. 8, 2020

Related U.S. Application Data

(63) Continuation of application No. 15/022,749, filed on Mar. 17, 2016, now Pat. No. 10,995,118, which is a continuation-in-part of application No. 14/388,869, filed as application No. PCT/DE2014/000477 on Sep. 23, 2014, now Pat. No. 9,464,118.

(30) Foreign Application Priority Data

Sep. 26, 2013 (DE) ............ 10 2013 016 002.2
Mar. 12, 2014 (DE) ............ 10 2014 003 262.0

(51) Int. Cl.
*C07K 7/08* (2006.01)
*G01N 33/68* (2006.01)
*A61K 38/12* (2006.01)
*A61K 38/10* (2006.01)
*A61K 38/16* (2006.01)
*A61K 38/00* (2006.01)

(52) U.S. Cl.
CPC .............. *C07K 7/08* (2013.01); *A61K 38/10* (2013.01); *A61K 38/12* (2013.01); *A61K 38/16* (2013.01); *G01N 33/6896* (2013.01); *A61K 38/00* (2013.01); *G01N 2333/4709* (2013.01); *G01N 2800/2821* (2013.01)

(58) Field of Classification Search
CPC .......... C07K 7/08; A61K 38/00; A61K 38/10; A61K 38/12; A61K 38/16; G01N 33/6896; G01N 2333/4709; G01N 2800/2821
See application file for complete search history.

(56) References Cited

FOREIGN PATENT DOCUMENTS

WO WO-0134631 A2 * 5/2001 ......... C07K 14/4711

OTHER PUBLICATIONS

Richman M et al. In vitro and mechanistic studies of an antiamyloidogenic self-assembled cyclic D,L-alpha-peptide architecture. J. Am. Chem. Soc. 2013, 135:3474-3484. (Year: 2013).*

* cited by examiner

*Primary Examiner* — Kimberly Ballard
(74) *Attorney, Agent, or Firm* — Norris McLaughlin, P.A.

(57) ABSTRACT

The invention relates to amyloid beta-binding peptides and the use thereof for the treatment and the diagnosis of Alzheimer's disease.

8 Claims, 8 Drawing Sheets

Specification includes a Sequence Listing.

AMYLOID-BETA-BINDING PEPTIDES AND THE USE THEREOF FOR THE TREATMENT AND DIAGNOSIS OF ALZHEIMER'S DISEASE

REFERENCE TO RELATED APPLICATION

This is a continuation application of Ser. No. 15/022,749, filed Mar. 17, 2016, currently pending. The subject matter of the aforementioned prior applications is hereby incorporated herein by reference.

The invention relates to amyloid beta-binding peptides and the use thereof for the treatment and the diagnosis of Alzheimer's disease.

PRIOR ART

Multivalent amyloid beta-binding polymeric substances, composed of multiple interconnected substances that on their own already have amyloid beta-binding properties, and the use of these substances, in particular in medicine, are known from the unexamined patent application WO 2013/150127 A2.

Given the demographic trend over the coming decades, the number of individuals suffering from age-related diseases will rise. In this regard, especially so-called Alzheimer's disease (AD, Latin: Morbus Alzheimer) shall be mentioned.

So far, no active ingredient or drug exists that acts against the causes of AD. The previously used and approved drugs alleviate some of the symptoms that occur with Alzheimer's disease. However, they are not able to slow the progression of the disease or provide a cure. Several substances exist that, in animal experiments, achieved successes in terms of prevention, but not (necessarily) in the treatment of AD. Active ingredients against neurodegenerative diseases are known from DE 10 2006 015 140 A1.

One trait of Alzheimer's disease is extracellular deposits of the amyloid beta peptide (A beta peptide, Aß, or Aß peptide). These deposits of the A beta peptide in plaque are typically found in the brains of AD patients post mortem. This is the reason why various forms of the A beta peptide, such as fibrils, are considered to be responsible for the development and progression of the diseases. Additionally, for some years now, the small, freely diffusable A beta oligomers have been regarded as the primary causative factor in the development and progression of AD.

The substances known from the prior art reduce the concentration of A beta monomers and/or oligomers in a wide variety of ways. For example, gamma-secretase modulators are known, which were used for prevention in animal experiments.

Various sequences of D-amino acids that bind to A beta peptides are known from WO 02/081505 A2. These sequences of D-amino acids bind to amyloid beta peptides with a dissociation constant ($K_D$ value) of 4 µM.

Hybrid compounds that are composed of aminopyrazoles and peptides and prevent A beta oligomerization are known from WO 2011/147797 A2.

Compounds that interact with A beta peptides are known from DE 10 2008 037 564 A1, DE 696 21 607 T2 or DE 10 2010 019 336 A1. The binding of a multivalent polymer to two binding partners is described in WO 2008/116293 A1.

In the case of many substances that showed positive results in animal experiments, this effect could not be confirmed in clinical human studies. In phase II and III clinical studies, only individuals who have been unambiguously diagnosed with AD are allowed to be treated. A minor reduction in the A beta monomer concentration will not be sufficient to prevent existing A beta oligomers from multiplying, such as by way of a prion-like mechanism. The multiplication of A beta oligomers or, even better, destruction of the same or rendering these ineffective, however, is absolutely necessary to influence the progression of the disease.

Until now, Alzheimer's disease is primarily diagnosed by way of neuropsychological tests, by conducting experiments on persons in which symptoms of dementia were detected. However, it is known that A beta oligomers, and the fibrils and plaque ensuing subsequently, develop in the brain of patients up to 20 years prior to the appearance of symptoms and can already have caused irreversible damage. However, to date, it is not possible yet to diagnose AD before symptoms appear.

As a result, there is a continued need for new compounds (active ingredients) that bind very specifically and with high affinity to A beta oligomers, and thereby prevent the multiplication thereof. These compounds should not produce undesirable side effects, and in particular cause no immune response. The compounds should additionally detect even small concentrations of toxic A beta oligomers, and thus also the small freely diffusable oligomers and completely destroy and/or prevent the (prion-like) multiplication of the same.

Furthermore, there is also a need for new compounds that can be used as probes for detecting and marking A beta oligomers, in particular when these oligomers occur only in small concentrations.

SUMMARY OF THE INVENTION

It is thus the object of the invention to provide compounds for

A) the causal treatment of Alzheimer's disease by these compounds preventing the formation of toxic amyloid beta oligomers, fibrils or aggregates, or by eliminating oligomers, fibrils or aggregates that have already developed, or by causing the detoxification of the same;

B) allowing Alzheimer's disease to be diagnosed by being able to use these compounds as probes for in vivo imaging.

This covers additional objects, such as the use of the compounds in medicine.

It is also an object of the invention to provide novel peptides, preferably derivatives of the D-enantiomeric D-peptide D3, which have more efficient properties than D3. The properties include, among other things, a higher binding affinity and specificity for A beta species, inhibition of A beta fibril formation, inhibition of A beta cytotoxicity, elimination or detoxification of A beta oligomers, fibrils and other aggregates, and conversion of A beta amyloid fibrils, protofibrils or oligomers into non-toxic, non-amyloidogenic species.

Hereafter, the terms "A beta," "amyloid beta," "amyloid ß" and "Aß" are used synonymously.

Solution to the Problem

The object is achieved by the peptide, the kit, and the composition according to the main claims, and by the methods and uses according to the additional independent claims.

Advantageous embodiments will be apparent from the respective claims dependent thereon.

DESCRIPTION OF THE INVENTION

A peptide according to the invention is a peptide comprising at least one amino acid sequence that binds to amyloid beta species, with this property being either preserved or amplified, and in which the free C-terminus, which is to say the C-terminal carboxyl group, is modified so that the C-terminus does not have a negative charge, but instead is neutral or has one or more positive charges.

The peptides according to the invention also include those peptides comprising at least one peptide binding to an amyloid-beta species, wherein the peptide includes a linear amino acid sequence which enables it to bind to A-beta, with this property being either preserved or amplified by the peptide being present in cyclized form as a result of a covalent bond of the two ends thereof.

The peptides according to the invention particularly advantageously also achieve the object by providing a peptide having no negative charge at the C-terminus. This advantageously causes the peptide to be able to bind with higher affinity to the target molecule as compared to a peptide comprising a carboxyl group at the free C-terminus. Peptides having a free, non-modified carboxyl group have a negative charge at this end in the physiological state.

In one embodiment of the invention, the peptides according to the invention are modified in the physiological state, in particular at pH 6 to 8, in particular 6.5 to 7.5, in particular at pH 6.0, pH 6.1, pH 6.2, pH 6.3, pH 6.4, pH 6.5, pH 6.6, pH 6.7, pH 6.8, pH 6.9, pH 7.0, pH 7.1, pH 7.2, pH 7.3, pH 7.4, pH 7.5, pH 7.6, pH 7.7, pH 7.8, pH 7.9 or pH 8.0, so that the C-terminus does not carry a negative charge, but instead is neutral or has one or more positive charges.

In one embodiment of the invention, the peptide is characterized in that an acid amide group is present at the free C-terminus in place of the carboxyl group. Instead of the carboxyl group (—COOH group), an acid amide group (—CONH$_2$ group) is thus provided at the C-terminus.

The peptide is thus particularly advantageously amidated at the free C-terminus.

This particularly advantageously achieves the further object that a peptide having no excess negative charge is present, which can bind with higher affinity to the target molecule and can be obtained in a simple manner.

In a further embodiment of the invention, the following further groups are present in place of the carboxyl group: COH, COCl, COBr, CONH-alkyl group, CONH-alkylamine group (positive net charge), and so forth, wherein there is no limitation to these, provided the technical teaching of the main claim is followed.

This object is achieved in particular by a peptide containing an amino acid sequence according to SEQ ID NO: 1 (RD2), SEQ ID NO: 2 (D3), SEQ ID NO: 3 (DB3), SEQ ID NO: 9 (D3r), SEQ ID NO: 10 (D3p), SEQ ID NO: 11 (D3a) and/or SEQ ID NO: 12 (D3p2k) and/or homologs, fragments, and parts thereof. These peptides are substance units (hereafter often referred to as "monomers") that bind to amyloid-beta species.

In one variant of the invention, monomers are used which bind to an A beta monomer and/or A beta oligomers and/or fibrils of the A beta peptide with a dissociation constant (Ko value) of no more than 500 µM, preferably 250, 100, 50 µM, particularly preferably 25, 10, 6 µM, and in particular 4, 2, 1 µM or sub-µM.

The object is, in particular, also achieved by polymers composed of two or more of the above-mentioned monomers or peptides according to the invention, in particular dimers of SEQ ID NO: 4 (RD2D3), SEQ ID NO: 5 (D3RD2), SEQ ID NO: 6 (D3D3), SEQ ID NO: 7 (RD2RD2) and/or SEQ ID NO: 8 (DB3DB3) and/or homologs thereof. The dimers are composed of two monomer units, which each bind to amyloid-beta species.

The polymers according to the invention, composed of monomers that, in turn, bind to A beta oligomers, exhibit clear, synergistic effects with respect to the selectivity and affinity thereof to the A beta oligomers, compared to the monomers. In other words, the polymers according to the invention, in particular the dimers, selected from the group consisting of SEQ ID NO: 4, SEQ ID NO: 5, SEQ ID NO: 6, SEQ ID NO: 7 and/or SEQ ID NO: 8, are superior to the monomers of which they are composed. Synergistic effects within the meaning of the present invention are effects that exhibit a higher selectivity and/or affinity with respect to relevant A beta species, in particular the $K_D$ value regarding the binding to A beta species compared to the individual monomer units.

In a further particularly advantageous embodiment of the invention, the polymers, and more particularly the dimers, (in vitro or in vivo) advantageously act more efficiently than the monomers in the animal model experiment.

In one variant of the invention, polymers are used which bind to an A beta monomer and/or A beta oligomers and/or fibrils of the A beta peptide, with a dissociation constant ($K_D$ value) of no more than 500 µM, preferably 250, 100, 50 µM, particularly preferably 25, 10, 1 µM, particularly preferably with a dissociation constant ($K_D$ value) of no more than 500 nM, 250, 100, 50, particularly preferably 25, 10, 1 nM, 500 µM, 100, 50, 25, 20, 15, 10, 9, 8, 7, 6, 5, 4, 3, 2, 1 µM to sub-µM, wherein any intermediate value is possible.

In one embodiment of the invention, the affinity is defined by way of the dissociation constant ($K_D$ value).

In an advantageous embodiment of the invention, the dissociation constant ($K_D$ value) of the peptide according to the invention is advantageously reduced compared to linear, binding peptides in which the free C-terminus, which is to say the C-terminal carboxyl group, has a negative charge. This is associated with improved properties of the peptides according to the invention, such as higher binding affinity and higher effectiveness in the decomposition and/or the prevention of the formation of toxic amyloid beta species. This applies in particular, but not exclusively, to a low $K_D$ value at the high-affinity site of the A beta (monomer, oligomer, and fibrils).

Fragments and parts advantageously exhibit a similar or identical effect as the peptides according to the invention.

In one variant of the invention, the peptides according to the invention, and more particularly the peptides according to SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11 and/or SEQ ID NO: 12 and the homologs, fragments or parts thereof, are substantially, preferably at least 50%, 60%, 75%, 80%, particularly preferably 85%, 90%, 95%, and in particular 96%, 97%, 98%, 99%, 100% composed of D-enantiomeric amino acids.

A polymer within the meaning of the invention is formed of 2, 3, 4, 5, 6, 7, 8, 9, 10, 11, 12, 13, 14, 15, 16, 17, 18, 19, 20 or more monomers that bind to amyloid beta species, and in particular to oligomers.

The polymer is in particular made of monomers selected from the group consisting of SEQ ID NO: 1, SEQ ID NO: 2, SEQ ID NO: 3, SEQ ID NO: 9, SEQ ID NO: 10, SEQ ID NO: 11 and/or SEQ ID NO: 12.

In one embodiment of the invention, the polymer may be selected from the group consisting of SEQ ID NO: 4, SEQ ID NO: 5, SEQ ID NO: 6, SEQ ID NO: 7 and/or SEQ ID NO: 8, and the homologs thereof, which on their own already bind to amyloid beta species.

In one embodiment of the invention, the peptides according to SEQ ID NOS: 1-12 are composed of D-enantiomeric amino acids.

In one embodiment of the invention, the peptides according to SEQ ID NOS: 1-12 are provided with an acid amide group at the free C-terminus. Monomers, such as D3, DB3 or RD2 according to SEQ ID NOS: 1-3, or D3r, Drp, D3a or D3(p2k) according to SEQ ID NOS: 9-12 are then amidated at position 12 at the free C-terminus. Polymers, such as RD2D3, D3RD2, D3D3, RD2RD2 or DB3DB3, are amidated at position 24 at the free C-terminus.

In a further embodiment of the invention, the peptides according to SEQ ID NOS: 1-12 are covalently bonded to each other at the free C-terminus and the free N-terminus and are then present in corresponding cyclized form. The ring closure also advantageously causes the carboxyl group at the free C-terminus to no longer be present.

The peptide according to the invention advantageously comprises an amino acid sequence in which the cyclization of the linear molecule has been carried out, for example, by way of a covalent bond of the first amino acid with the last amino acid, such as by way of a condensation reaction. Other options for cyclization exist, of course, for example by coupling other amino acids to each other. The coupling of the second amino acid to the last amino acid shall only be mentioned by way of example. Any possible other coupling is equally conceivable.

If the first and last amino acids of the peptide are coupled to each other, this advantageously results in no open ends being present in the peptide chain (amino acid sequence).

A further result of this measure is that all peptides having linear amino acid sequences that, after cyclization, yield the same, no longer distinguishable amino acid order, are identical in this regard.

Example

The linear amino acid sequence of the known peptide D3 is rprtrlhthrnr. The corresponding cyclized peptide "cD3" linked between the N-terminal amino group and the C-terminal carboxyl group by an amide bond is no longer distinguishable from the cyclized peptides prtrlhthrnrr, rtrlhthrnrrp, trlhthrnrrpr, rlhthrnrrprt, lhthrnrrprtr, hthrnrrprtrl, thrnrrprtrlh, hrnrrprtrlht, rnrrprtrlhth, nrrprtrlhthr, or rrprtrlhthrn. It is still possible to derive the cD3 from each of these sequences.

The effects claimed according to the invention of higher affinity and effectiveness moreover occur with respect to one, preferably even with respect to each, linear binding peptide from which a cyclized or otherwise modified peptide according to the invention can be derived.

Otherwise, the production of cyclized peptides is state of the art and can be carried out, for example, according to the methods as described in DE 102005049537 A1.

The cyclization via the first and last amino acids of the peptide advantageously also means that there are no longer any "open" ends of the peptide chain, which often represent points of attack for peptide-decomposing activities in cells, animals or humans, such as by way of aminopeptidases and carboxypeptidases.

Using cyclized monomers according to the invention, such as cD3, cRD2 and so forth, or cyclized polymers, such as cRD2D3, cD3D3, cDB3DB3 and so forth, also advantageously achieves that, as a side effect, these cyclized peptides according to the invention are also potentially not easily degraded, although this effect is not decisive. Incidentally, as was shown, this effect also applies only for the case of a head-to-tail or tail-to-head cyclization, in which the two ends of the linear peptide are correspondingly coupled to each other.

In a further embodiment of the invention, the polymers are composed of identical monomers, such as D3, RD2 or DB3, or of a combination of 2, 3, 4, 5, 6, 7, 8, 9 or 10 different, varying monomers as mentioned above, as so-called combination polymers. Some of the monomers can also be identical. The number of identical monomers in the combination polymers is freely selectable.

Polymers can be produced by chemical synthesis or peptide synthesis, for example.

In one embodiment of the invention, the monomers are covalently bonded to each other. In a further embodiment, the monomers are not covalently bonded to each other.

A covalent bond or coupling of the monomer units within the meaning of the invention is present if the peptides are linearly coupled to each other head to head, tail to tail, or head to tail, with or without interposed linkers or linker groups.

A non-covalent bond within the meaning of the invention exists if the monomers are coupled to each other via biotin and streptavidin, in particular streptavidin tetramer, for example.

In one variant of the present invention, the monomers can be linearly coupled to each other, in particular as described above. In another variant, the monomers are coupled to each other in a branched manner to obtain the polymer according to the invention.

According to the invention, the branched polymer can be a dendrimer in which the monomers are covalently or not covalently coupled to each other.

Alternatively, the monomers can also be coupled to a platform molecule (such as PEG or sugar) and thus form a branched polymer.

Alternatively, combinations of these options are also possible.

Monomers and polymers are hereinafter referred to as peptides according to the invention.

In one variant of the invention, a peptide is used having the amino acid sequence according to SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11 and/or SEQ ID NO: 12 and/or homologs thereof having an identity of 50%.

Within the meaning of the invention, "homologous sequences" or "homologs" shall mean that an amino acid sequence has an identity of at least 50, 55, 60, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100% with one of the above-mentioned amino acid sequences of the monomers. Instead of the term "identity," the terms "homologous" or "homology" are used as synonyms in the present description. The identity between two nucleic acid sequences or polypeptide sequences is calculated by comparison with the aid of the BESTFIT program, based on the algorithm by Smith, T. F. and Waterman, M. S (Adv. Appl. Math. 2: 482-489 (1981)), setting the following parameters for amino acids: Gap creation penalty: 8 and Gap extension penalty: 2; and setting the following parameters for nucleic acids: Gap creation penalty: 50 and Gap extension penalty: 3. The identity between two nucleic acid sequences or polypeptide sequences is preferably defined by the identity of the nucleic acid sequence/polypeptide sequence over the entire respective sequence length, as it is calculated by comparison with the aid of the GAP program, based on the algorithm by Needleman, S. B. and Wunsch, C D. (J. Mol. Biol. 48:

443-453), setting the following parameters for amino acids: Gap creation penalty: 8 and Gap extension penalty: 2; and setting the following parameters for nucleic acids: Gap creation penalty: 50 and Gap extension penalty: 3.

Two amino acid sequences are identical within the meaning of the present invention if they have the same amino acid sequence.

In one variant, homologs shall be understood to mean the corresponding retro-inverse sequences of the above-mentioned monomers. According to the invention, the term "retro-inverse sequence" denotes an amino acid sequence that is composed of amino acids in the enantiomeric form (inverse: chirality of the alpha carbon atom is inverted), and in which additionally the sequence order was reversed compared to the original amino acid sequence (retro=reverse).

In a further variant, the peptides according to the invention bind to parts of the amyloid beta peptide.

In a further variant, the peptides according to the invention have sequences that differ from the indicated sequences by up to three amino acids.

Moreover, peptides containing the above-mentioned sequences are also used as sequences.

In a further variant, the peptides comprise fragments of the above-mentioned sequences or comprise homologous sequences with respect to the above-mentioned sequences.

According to the invention, the peptide is a peptide for use in medicine, and preferably for treating Alzheimer's disease.

In one embodiment of the present invention, the peptide is substantially composed of D-amino acids.

Within the meaning of the present invention, the expression "substantially composed of D-enantiomeric amino acids" shall mean that at least 50%, 60%, preferably 75%, 80%, particularly preferably 85%, 90%, 95%, and in particular 96%, 97%, 98%, 99% or 100% of the monomers to be used according to the invention will be D-enantiomeric amino acids.

In one embodiment of the present invention, the monomer peptides according to the invention are derivatives of the D-enantiomeric D-peptide D3. Derivatives within the meaning of the invention are peptide sequences that are derived from D3 and are obtained according to one of the three following methods:

a) changing the order and/or number of the amino acid building blocks in D3. Only amino acids that are present in the D3 sequence are used.

d) deleting 1, 2, 3, 4, 5, 6, 7, 8, 9, 10 or 11 amino acids of the D3 sequence.

c) exchanging 1, 3, 4, 5, 6 or 6 amino acids with other amino acids, preferably D-enantiomers.

A further variant concerns a peptide according to the invention for inhibiting the fibril formation of amyloid beta oligomers. The peptides according to the invention detoxify the A beta oligomers or polymers formed thereof, and fibrils, by binding thereto, thus converting them into non-toxic compounds. The present invention thus also relates to a method for detoxifying the A beta oligomers, or polymers or fibrils formed thereof.

In one embodiment, the invention also relates to peptides according to the invention that are linked to another substance.

The linkage within the meaning of the invention is a chemical bond as it is defined in Römpp Chemie Lexikon (chemistry encyclopedia), 9th edition, volume 1, page 650 et seq., Georg Thieme Verlag, Stuttgart, preferably a principal valence bond, and more particularly a covalent bond.

The substances, in one variant, are pharmaceutical products or active ingredients, defined according to German Drug Act § 2 or § 4 (19), as amended in September 2012. In one alternative, active ingredients are therapeutically active substances that are used as active pharmaceutical substances. Preferably anti-inflammatory agents are used.

In a further variant, the substances are compounds that enhance the effect of the peptides.

In one alternative, such compounds are aminopyrazole and/or aminopyrazole derivatives. Aminopyrazole derivatives within the meaning of the invention is 3-aminopyrazole-5-carboxylic acid or 3-nitropyrazole-5-carboxylic acid and all derivatives in which the heterocyclic CH group was replaced with —CR— or —N or —O— or —S—, and all peptidic dimers, trimers or tetramers derived therefrom, preferably aminopyrazole trimer.

In a further alternative, they are compounds that improve the solubility of the peptides and/or the passage thereof through the blood brain barrier.

In one alternative, the peptides according to the invention have any arbitrary combination of at least two or more features of the above-described variants, embodiments and/or alternatives.

Within the scope of the invention, it was furthermore found that the peptides modified according to the invention have a higher binding affinity to A beta species, and particularly the especially toxic amyloid beta oligomers, than linear binding peptides in which the free C-terminus, which is to say the C-terminal carboxyl group, is not modified and correspondingly has a negative charge. This means that the $K_D$ value is lower in the peptides according to the invention than in linear peptides in which the free C-terminus, which is to say the C-terminal carboxyl group, is not modified and correspondingly has a negative charge.

In a further preferred embodiment of the invention, the binding affinity of the peptides modified according to the invention having no negative charge at the C-terminus, compared to linear peptides having a negative charge at the C-terminus, but otherwise having the same amino acid sequence, is thus increased by 1%, 2, 3, 4, 5, 6, 7, 8, 9, in particular 10%, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, in particular 100%, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, in particular 200%, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, in particular 300%, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, in particular 400%, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, advantageously even 500%, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, particularly advantageously 600%, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, particularly advantageously 700%, 701, 702, 703, 704, 705, 706, 707, 708, 709, 710, 711, 712, 713, 714, 715, 716, 717, 718, 719, 720, 721, 722, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 753, 754, 755, 756, 757, 758, 759, 760, 761, 762, 763, 764, 765, 766, 767, 768, 769, 770, 771, 772, 773, 774, 775, 776, 777, 778, 779, 780, 781, 782, 783, 784, 785, 786, 787, 788, 789, 790, 791, 792, 793, 794, 795, 796, 797, 798, 799, likewise particularly advantageously 800%, 801, 802, 803, 804, 805, 806, 807, 808, 809, 810, 811, 812, 813, 814, 815, 816, 817, 818, 819, 820, 821, 822, 823, 824, 825, 826, 827, 828, 829, 830, 831, 832, 833, 834, 835, 836, 837, 838, 839, 840, 841, 842, 843, 844, 845, 846, 847, 848, 849, 850, 851, 852, 853, 854, 855, 856, 857, 858, 859, 860, 861, 862, 863, 864, 865, 866, 867, 868, 869, 870, 871, 872, 873, 874, 875, 876, 877, 878, 879, 880, 881, 882, 883, 884, 885, 886, 887, 888, 889, 890, 891, 892, 893, 894, 895, 896, 897, 898, 899, likewise particularly advantageously 900%, 901, 902, 903, 904, 905, 906, 907, 908, 909, 910, 911, 912, 913, 914, 915, 916, 917, 918, 919, 920, 921, 922, 923, 924, 925, 926, 927, 928, 929, 930, 931, 932, 933, 934, 935, 936, 937, 938, 939, 940, 941, 942, 943, 944, 945, 946, 947, 948, 949, 950, 951, 952, 953, 954, 955, 956, 957, 958, 959, 960, 961, 962, 963, 964, 965, 966, 967, 968, 969, 970, 971, 972, 973, 974, 975, 976, 977, 978, 979, 980, 981, 982, 983, 984, 985, 986, 987, 988, 989, 990, 991, 992, 993, 994, 995, 996, 997, 998, 999, or even by 1000%, or even by 10000% or even by up to 100000% or 1000000%, wherein any intermediate value is possible. This applies in particular, but not exclusively, to an increased affinity with the high-affinity site of the A beta (monomer, oligomer, fibrils and so forth).

This is indicated by a correspondingly reduced $K_D$ value. Compared to a linear, binding peptide having a negative charge at the C-terminus, the $K_D$ value, as a measure of the binding affinity of the peptide modified according to the invention to amyloid beta species, and in particular to amyloid beta oligomers, is reduced by 1%, 2, 3, 4, 5, 6, 7, 8, 9, in particular 10%, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, in particular 99.1, 99.2, 99.3, 99.4, 99.5%, 99.6, 99.7, 99.8, 99.9 to 99.99, or even 99.999%, wherein any intermediate value is possible.

Advantageously, these lower $K_D$ values refer in particular, but not exclusively, to the high-affinity site of A beta species (monomer, oligomer, fibrils, and so forth).

Peptides modified according to the invention can therefore be used more efficiently as probes for diagnostic purposes than linear, binding peptides having a negative charge at the free C-terminus, in particular more efficiently than the linear peptide analogs thereof having an identical amino acid sequence.

However, they can in particular also be used more efficiently as therapeutic agents than linear, binding peptides having a negative charge at the free C-terminus, and in particular more efficiently than the linear peptide analogs thereof having an identical amino acid sequence.

In the direct comparison of a peptide modified according to the invention to a peptide having a negative charge at the C-terminus, the peptide according to the invention performs better in terms of affinity and effectiveness.

The reason is that, within the scope of the invention, it was further recognized that the peptides modified according to the invention additionally prevent the formation of particularly toxic amyloid beta oligomers, or cause the destruction and/or final toxification thereof, with higher effectiveness or efficiency than peptides having a negative charge at the free C-terminus, in particular than the peptide analogs thereof having an identical amino acid sequence. This effectiveness is in particular increased by 1%, 2, 3, 4, 5, 6, 7, 8, 9, in particular 10%, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 99.9, and particularly advantageously even by 100%.

For this purpose, a sample comprising different Aβ conformers is fractionated, for example, in the simplest case as an experiment. In each fraction, different conformers, such as monomers, oligomers, fibrils or higher aggregates, are enriched corresponding to the fractionating step and can then be exactly determined.

The expression "exactly determined" comprises a calibration step during the fractionating with molecules of a known type and behavior. After fractionating, only a certain type of conformers of the Aβ is present in each fraction, such as monomers, oligomers or fibrils, and so forth.

For example, the conformers are separated according to the s value or sedimentation coefficient thereof in density gradient centrifugation, serving as the fractionating step. Molecules of differing sizes can have an identical hydrodynamic radius, but nonetheless have different s values and are separated according to these. Calibration using molecules having a known s value allows the Aβ conformers obtained by way of density gradient centrifugation to be exactly determined according to the s value thereof.

Thereafter, the resultant fractions are treated with and without an active ingredient and determined by way of RP-HPLC, for example. In this way, it is possible to determine the effectiveness of the active ingredient.

A further method is described hereafter. The so-called QIAD (quantitative determination of interference with Aß aggregate size distribution) test can be used for the quantitative analysis of active ingredients. The method for quantitatively analyzing the influence of an active ingredient on the particle size distribution of amyloid peptides and/or proteins in a sample comprises the following steps. First, A beta is allowed to aggregate under controlled conditions, whereby different A beta aggregates develop. The conditions are selected so that a particularly high number of small, especially cytotoxic A beta oligomers are formed. Next, the substance to be examined, such as one of the modified peptides according to the invention, is added to the sample. The active ingredient changes the particle size distribution in the sample. This change is established quantitatively. The change is a measure of the reduction, or even of the complete elimination, of certain toxic species of a certain particle size. The QIAD method is used to measure the increase or the decrease in A beta aggregates having a certain particle size. While some A beta aggregates having a certain size were initially present in the sample, these are reduced, or even completely eliminated, under the influence of the active ingredient. Other particle sizes increase or remain constant under the influence of the active ingredient. The particles that are formed from the A beta are preferably separated from each other according to the hydrodynamic radius of the particles. In this way, advantageously a multitude of fractions are obtained from the sample. The particles of amyloid peptides and/or proteins having a certain aggregate size are enriched in the fractions. This separation of the particles can be carried out by way of density gradient centrifugation. The fractions are spatially separated from each other, such as by way of pipetting them off. Finally, the concentration of A beta in the respective fraction is determined by completely denaturing the A beta species during a reverse phase (RP-) HPLC carried out subsequent to the fractionating. The denaturing of the aggregates can take place completely, for example using 30% acetonitrile and 0.1% trifluoroacetic acid at a column temperature of 80° C., and separating according to hydrophobicity on a C8 column. Eluting A beta is detected by way of UV absorption at 215 nm. The peak area integration can be performed with Agilent ChemStation software. By considering the resultant values in the computation with a previously conducted calibration, it is possible to calculate the concentration of A beta present in the particular fraction. Depending on the fraction, the mean value from multiple, for example six, experiments conducted independently of one another can be calculated with the resulting standard deviation. The advantage of HPLC analysis is that detection is very sensitive (such as approximately 20 nM or 1.8 ng Aß1-42) and quantification is reliable independently of the state of aggregation and the solvent. A decisive advantage of the method lies in the coupling of density gradient centrifugation and reverse phase HLPC, which allows also Aß oligomers to be reliably quantified.

The effect according to the invention of increased effectiveness in the elimination (or the formation) of amyloid beta species, and in particular amyloid beta oligomers, can take place with one of these methods, but not exclusively with these methods.

In a particularly preferred embodiment of the invention, the described effects of increased affinity and effectiveness of elimination, and detoxification (or formation) also take place in vitro and/or in vivo.

The invention further relates to a peptide according to the invention for binding to A beta peptides.

The invention moreover relates to a method for producing the peptide according to the invention by way of peptide synthesis, as known to a person skilled in the art, for example, organic synthesis methods for arbitrary low-molecular-weight compounds and/or mutagenesis and recombinant production.

The invention also relates to a composition containing the peptide according to the invention, in particular for treating Alzheimer's disease.

The present invention further relates to a composition containing the peptide according to the invention, in particular for preventing toxic A beta oligomers, or for destroying polymers or fibrils formed thereof.

The "composition" according to the invention can be a vaccine, a drug (such as in tablet form), an injection solution, a food or dietary supplement, for example, containing the peptide according to the invention in a formulation to be produced based on expert knowledge.

The invention further relates to a kit containing the peptide according to the invention. In such a kit, the peptides according to the invention can be packaged in containers, optionally with/in buffers or solutions. All components of the kit may be packaged in the same container or separately from each other. The kit can moreover include instructions for the use thereof. Such a kit can include, for example, the according to the invention in an injection vial having a stopper and/or septum. A disposable syringe can also be included therein, for example.

The present invention further relates to the use of the peptide according to the invention as a probe for identifying and qualitatively and/or quantitatively determining amyloid beta oligomers or fibrils.

The present invention further relates to a probe, containing the peptide according to the invention for identifying and qualitatively and/or quantitatively determining amyloid beta oligomers.

Such probes are of great importance in enabling early diagnosis of AD. Early diagnosis allows the disease to be counteracted at a very early stage.

Such molecular probes contain the polymer according to the invention and optionally dyes, fluorescent dyes, radioactive isotopes (PET and the like), gadolinium (MRI), and alternative substances suitable for the imaging of probes and can be injected in the patient, for example intravenously. After passing the blood-brain barrier, the probes can bind to A beta oligomers and/or plaque. The A beta oligomers and/or plaque thus marked can be rendered visible using imaging processes, such as SPECT, PET, CT, MRI, proton MR spectroscopy and so forth.

The invention further relates to the use of the peptide for preventing amyloid beta oligomers and/or amyloid beta peptide aggregates and/or amyloid beta fibrils.

The peptide according to the invention is also used to detoxify toxic amyloid beta oligomers and/or aggregates. It is used in particular to bind to amyloid beta oligomers and/or aggregates and thus form amorphous, non-toxic aggregates.

It was found that, when Aß oligomers are already present, the goal of a treatment must be to address these with substances that have the highest possible affinity to A beta. De facto, the affinity cannot be high enough, and the corresponding dissociation constant of the peptide according to the invention is then in the sub-µM range, better even in the pM range or even lower.

It was found within the scope of the invention that A beta monomers, as building blocks of the A beta oligomers, are continuously created in the human body and presumably are not toxic per se. There is even the possibility that monomers have a positive function. A beta monomers are able to randomly agglomerate as a function of the concentration thereof. The concentration is dependent on the formation and decomposition rate thereof. If the concentration of A beta monomers in the body rises with increasing age, spontaneous agglomeration of the monomers to form A beta oligomers is increasingly likely. It is possible that the A beta oligomers thus created multiply analogously to the prions and ultimately lead to Alzheimer's disease.

It was furthermore found that an important difference between the prevention and treatment of, or even a cure for, AD lies in the fact that prevention can potentially already be achieved by preventing the formation of the first A beta oligomers. Just a few A beta ligands are sufficient for this purpose, which have low affinity and are selective with respect to the A beta oligomers.

The formation of the A beta oligomers from multiple monomers is a reaction of a high order and is thus dependent to a high degree on the A beta monomer concentration. As a result, a small reduction in the active A beta monomer concentration thus already prevents the initial A beta oligomers from forming. The treatment concepts and substances previously in development, which were of a more preventive nature, are presumably based on this mechanism.

However, an entirely different situation must be assumed for the treatment of AD. A beta oligomers, or potentially even larger polymers or fibrils, are already present then, which multiply by way of prion-like mechanisms. This multiplication, however, is a reaction of a lower order and is then almost independent of the A beta monomer concentration.

If A beta oligomers have already been created, the goal of a treatment must be to address these with substances that have the highest possible affinity to Aß oligomers and/or to eliminate these particularly efficiently and/or to prevent formation particularly efficiently or detoxify the same. The corresponding dissociation constant would have to be in the sub-µM, nM or pM range, or even lower.

These requirements in regard to the diagnosis (probes) and treatment of Alzheimer's disease are met with the provision of the peptides according to the invention. The peptides according to the invention, in the spirit of the diagnosis and/or treatment, bind the amyloid beta species, and in particular the A beta oligomers, with an accordingly low dissociation constant. The invention accordingly further relates to the use of the peptides according to the invention as a therapeutic agent for Alzheimer's disease.

The peptides according to the invention bind particularly well to A beta oligomers, and in particular to soluble A beta oligomers.

A high specificity for and/or affinity to the target molecule of the peptides according to the invention causes particularly strong binding of the peptides according to the invention to the target molecules. The formed complexes thus have a lower dissociation constant (KD value).

Using the thioflavin T assay, it was possible to show that the peptides according to the invention very efficiently inhibit the fibril formation of A beta peptides, especially the peptides of SEQ ID NOS: 1-12, in particular SEQ ID NO: 4, SEQ ID NO:5, SEQ ID NO: 6, SEQ ID NO: 7 and/or SEQ ID NO: 8.

The invention further relates to the use of the peptides according to the invention in a method for treating (in vitro, ex vivo) blood, blood products and/or organs, characterized in that the blood, the blood products and/or the organs are derived from the human or animal body and A (amyloid) beta oligomers are removed and/or detoxified.

The invention will be described in more detail hereafter based on exemplary embodiments and the accompanying figures, without thereby limiting the invention.

DETAILED DESCRIPTION OF THE INVENTION

Figure 1:
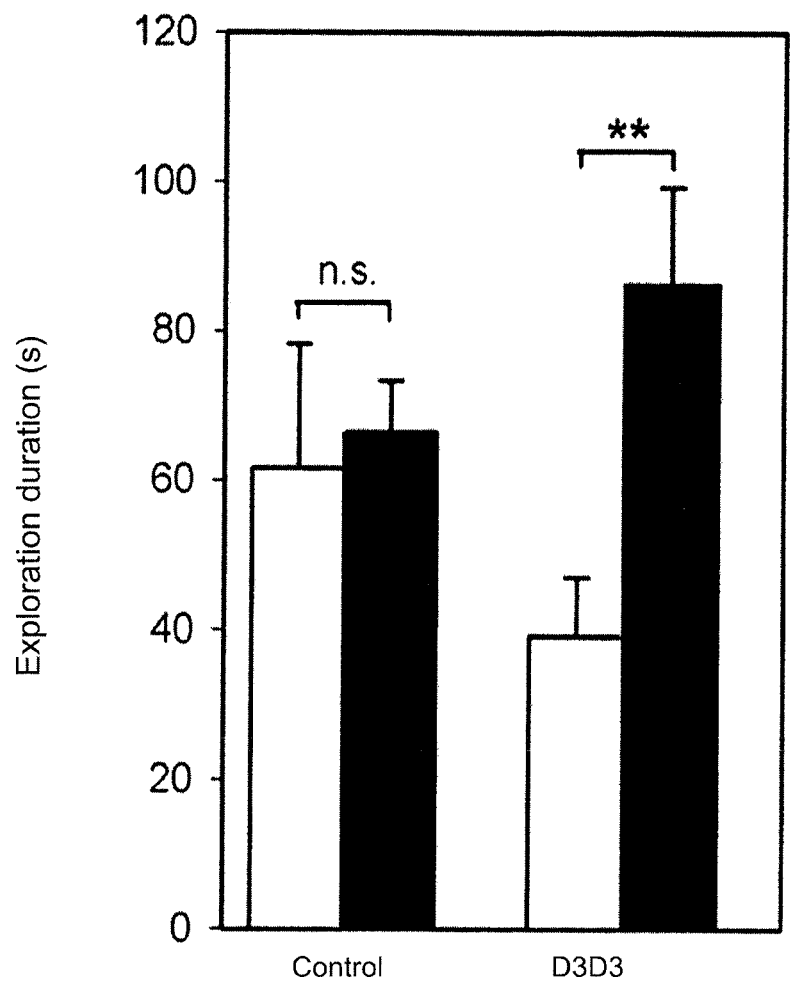
FIG. 1: Object recognition test

The QIAD (quantitative determination of interference with Aß aggregate size distribution) test was used for the quantitative analysis of active ingredients. The method for quantitatively analyzing the influence of an active ingredient on the particle size distribution of amyloid peptides and/or proteins in a sample comprises the following steps. First, A beta is allowed to aggregate under controlled conditions, whereby different A beta aggregates develop. For the result summarized in Table 1, the conditions were selected so that a particularly high number of small, especially cytotoxic A beta oligomers were formed. Next, the substance to be examined, such as one of the aforementioned D-enantiomeric peptides, is added to the sample. The active ingredient changes the particle size distribution in the sample. This change is established quantitatively. The change is a measure of the reduction, or even of the complete elimination, of certain toxic species of a certain particle size. The QIAD method is thus used to measure the increase or the decrease in A beta aggregates having a certain particle size. While some A beta aggregates having a certain size were initially present in the sample, these are reduced, or even completely eliminated, under the influence of the active ingredient. Other particle sizes increase or remain constant under the influence of the active ingredient. The particles that are formed from the A beta are preferably separated from each other according to the hydrodynamic radius of the particles. In this way, advantageously a multitude of fractions are obtained from the sample. The particles of amyloid peptides and/or proteins having a certain aggregate size are enriched in the fractions. This separation of the particles can be carried out by way of density gradient centrifugation. The fractions are spatially separated from each other, such as by way of pipetting them off. Finally, the concentration of A beta in the respective fraction is determined by completely denaturing the A beta species during a reverse phase (RP-) HPLC carried out subsequent to the fractionating. The denaturing of the aggregates can take place completely, for example using 30% acetonitrile and 0.1% trifluoroacetic acid at a column temperature of 80° C., and separating according to hydrophobicity on a C8 column. Eluting A beta is detected by way of UV absorption at 215 nm. The peak area integration can be performed with Agilent ChemStation software. By considering the resultant values in the computation with the previously conducted calibration, it is possible to calculate the concentration of A beta present in the particular fraction. Depending on the fraction, the mean value from multiple, for example six, experiments conducted independently of one another should be calculated with the resulting standard deviation. The advantage of HPLC analysis is that detection is very sensitive (such as approximately 20 nM or 1.8 ng Aß1-42) and quantification is reliable independently of the state of aggregation and a solvent. A decisive advantage of the method lies in the coupling of density gradient centrifugation and reverse phase HLPC, which allows also Aß oligomers to be reliably quantified.

The results are summarized in Table 1. They show that the substances eliminate oligomers particularly efficiently.

TABLE 1

| | Substance/Peptide | QIAD: reduction of oligomers in % |
|---|---|---|
| 1 | D3 amidated | 56 |
| 2 | RD2 amidated | 78 |
| 3 | D3D3 amidated | 98 |
| 4 | RD2RD2 amidated | 97 |
| 5 | RD2D3 amidated | 100 |
| 6 | D3RD2 amidated | 88 |

Each of the substances was used in a concentration of 32 µg/ml.

The results furthermore show that the tested dimers according to the invention have a synergistic effect compared to the monomers used at the same dosage.

Hereafter, several in vivo data for the employed peptides will be presented, which demonstrate the efficacy of the polymers according to the invention, in particular that of the dimers, and in particular that of the dimers according to the invention according to SEQ ID NOS: 4-8.

In animal experiments conducted on various transgenic mouse models (Table 2), it was shown that all previously tested amidated peptides are active in vivo.

FIG. 1: Here, the result of the so-called "object recognition test" (ORT) is shown. Animals treated with D3D3 (amidated) (details in Table 2) and animals treated with placebo were placed individually and separately from each other in a box in which two objects were located. After the animals had time to explore both objects, the animals were removed from the box again and not placed back in there until 24 hours later. Before that, however, one object was replaced with a new object different therefrom. Animals having memory now preferably explore the new object. Animals having no memory of having stayed in the box 24 hours earlier spend the same amount of time exploring the old object and the new object. The time that the animal spends with the old object (white bars) and the new object (black bars) is measured in seconds. It is clearly apparent that the animals treated with the placebo spend the same amount of time with the new and the old objects. Animals treated with D3D3, however, spend much more time with the new object. Thus, only the animals treated with D3D3 show a functioning memory in the test.

Figure 2:
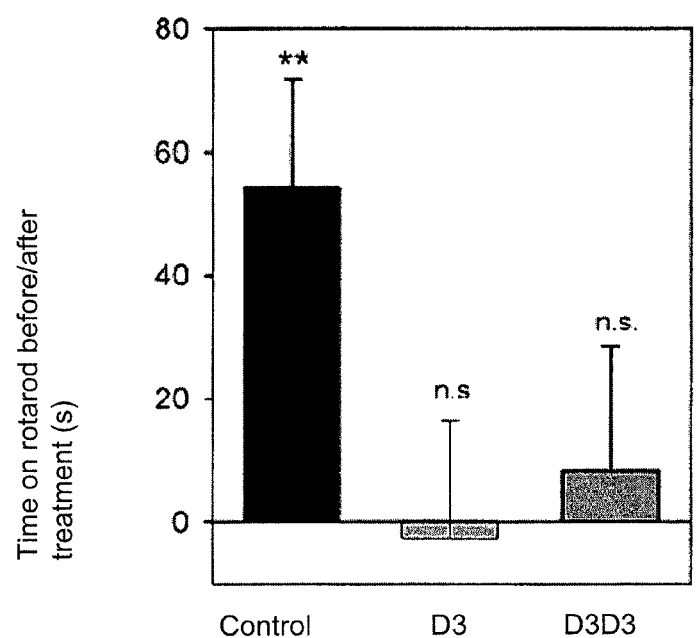
FIG. 2: RotaRod

FIG. 2: The so-called "rotarod" test is used to measure how long an animal is able to balance on a rotating rod before falling off. This allows the animal's neuromotor performance to be measured. The longer the animal is able to balance, the less strongly the motor neurons are affected by the phenotype of neurodegeneration. The measurement was carried out prior to and after the treatment (treatment details are provided in Table 2). The difference between before and after treatment is plotted in seconds. The positive value for the control group (black bar) indicates that the untreated animals exhibited less degeneration prior to treatment than after the treatment with the placebo. As expected, the degeneration has thus progressed. The animals treated with D3 (amidated) and D3D3 (amidated), however, exhibited no worsening of the neuromotor symptoms. Thus, the treatment slowed, or even stopped, the neurodegeneration in both instances.

Figure 3:
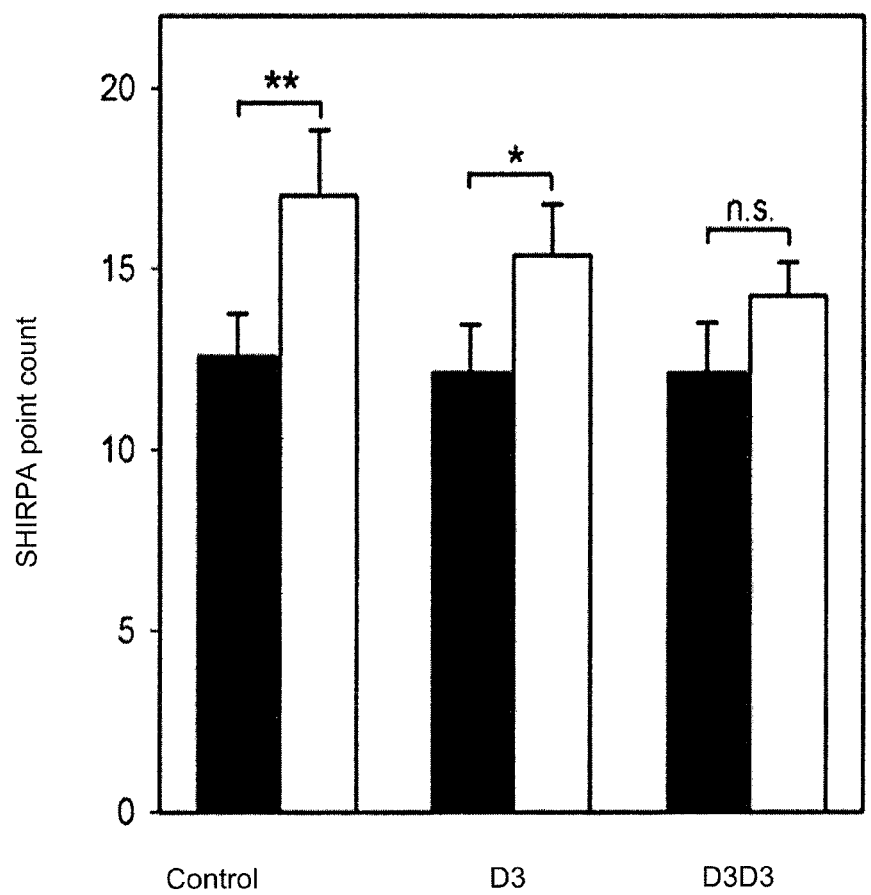
FIG. 3: SHIRPA

FIG. 3: The SHIRPA test is a test where a number of characteristics, including reflexes, are tested. Each characteristic is assessed separately from the others, and points are awarded in each case. The higher the number of points, the more progressed the phenotype, which is to say the neurological damage, is. The SHIRPA test was measured prior to (black bars) and after (white bards) the treatment (treatment details are provided in Table 2). It is apparent that the animals treated with D3D3 (amidated) showed no significant worsening of the SHIRPA value. The animals treated with D3 (amidated) and with the placebo, however, showed a more or less pronounced worsening of the SHIRPA value. D3D3 thus acts more efficiently than D3.

Figure 4:
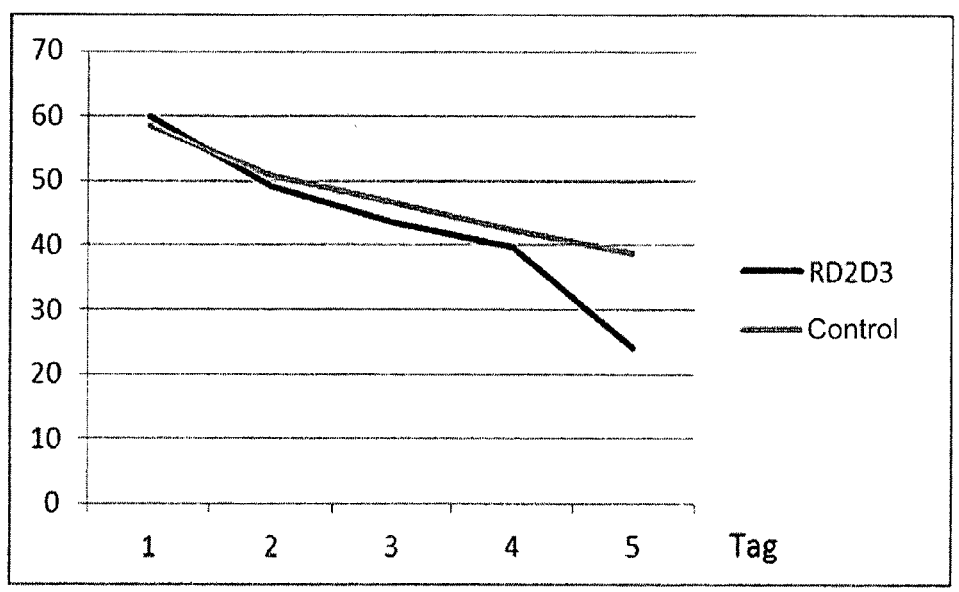
FIG. 4: Morris water maze

FIG. 4: The so-called "Morris water maze" is used to measure the spatial memory of animals. The time is measured in seconds that the animal requires to locate a platform hidden closely beneath the water surface in a water tank. This is measured in several experiments per day on several consecutive days. A statistical evaluation then shows whether the learning in terms of locating the platform was better among the treated animals compared to the control group. The search time is plotted in seconds on five consecutive days. The learning of animals treated with RD2D3 (amidated) was significant.

Figure 5:
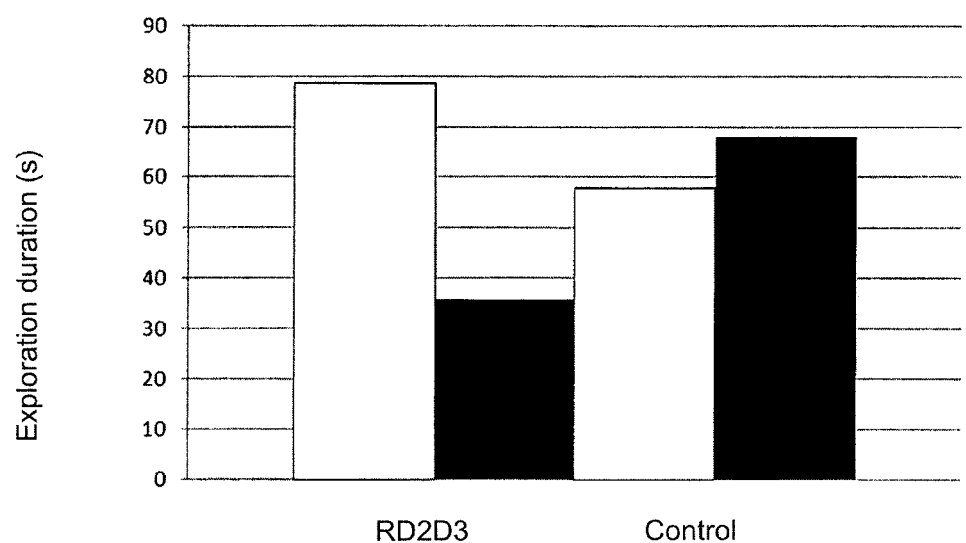
FIG. 5: Object recognition

FIG. 5: Here, the result of the so-called "object recognition test" (ORT) is shown. Animals treated with RD2D3 (amidated) (details in Table 2) and animals treated with placebo were placed individually and separately from each other in a box in which two objects were located. After the animals had time to explore both objects, the animals were removed from the box again and not placed back in there until 24 hours later. Before that, however, one object was replaced with a new object different therefrom. Animals having memory now preferably explore the new object. Animals having no memory of having stayed in the box 24 hours earlier spend the same amount of time exploring the old object and the new object. The time that the animal spends with the old object (black bars) and the new object (white bars) is measured in seconds. It is clearly apparent that the animals treated with the placebo spent the same amount of time with the new and the old objects. Animals treated with RD2D3, however, spend much more time with the new object. Thus, only the animals treated with RD2D3 showed a functioning memory in the test.

The amidated forms of D3 and D3D3 are able to stop the progression of the phenotype in TBA 2.1 mice during the treatment period of 4 weeks (see also FIG. 2).

In particular, it was possible to confirm that the double peptide D3D3 (amidated) acts more efficiently than the simple peptide D3 (amidated), and more particularly in the SHIRPA test, likewise in the TBA 2.1 animal model (FIG. 3). D3D3 was able to demonstrate in the SweDI mouse model that it considerably improves cognition (in the object cognition test, FIG. 1) compared to untreated mice. RD2D3 (amidated) is likewise able to improve the cognition of SweDI mice, which was demonstrated both in the Morris water maze (FIG. 4) and in the object recognition test (FIG. 5).

FURTHER EXEMPLARY EMBODIMENTS

The following steps refer both to affinity studies and to studies on the decomposition of particularly toxic amyloid beta oligomers.

Production of Aß Monomers, Oligomers, and Fibrils 1 mg lyophilized Aß1-42 and N-terminal biotinylated Aß1-42 were each dissolved in 1 ml 100% hexafluoroisopropanol (HFIP) and dissolved overnight at room temperature. For the oligomer and fibril preparation, non-biotinylated Aß was used with N-terminal biotinylated Aß at a ratio of 1:10 and the HFIP was evaporated (Concentrator 5301 from Eppendorf). The resultant Aß film, at a final concentration of 80 µM, was placed in sodium phosphate buffer (10 mM, pH 7.4) and incubated (RT, 600 rpm). The incubation time was 3 h for the oligomer preparation, and 24 h for the fibril preparation. 100% N-terminal biotinylated Aß1-42 without incubation was used for the preparation of monomers.

Density Gradient Centrifugation

The density gradient centrifugation was carried out subsequent to the Aß preparation to purify the respective Aß species according to the size of the same. An iodixanol gradient in 10 mM sodium phosphate buffer, pH 7.4 with rising concentrations from 50% to 5% v/v iodixanol was used for this purpose. 100 µl of the Aß sample was applied and separated by way of ultracentrifugation (3 h, 4° C., 259000 g). Subsequently, the gradient was fractionated into 14 fractions, 140 µl each. Monomeric Aß are present in the first two top fractions, Aß oligomers in fractions 4 to 6, and Aß fibrils in fractions 1 to 13.

Immobilization for Surface Plasmon Resonance (SPR) Spectroscopy A T200 from Biacore (GE Healthcare) was used for SPR spectroscopy. The Aß species purified by way of density gradient centrifugation were directly immobilized on a sensor chip (Series S Sensor Chips SA) according to the manufacturer's instructions by way of biotin-streptavidin coupling. 1×PBS was used as the running buffer. Loading took place at 25° C. and a flow rate of 5 µl/min. Subsequently, the flow cells were freed from non-specifically bound ligand overnight at a steady flow of 30 µl/min.

Binding Kinetics

Binding kinetics were likewise measured by way of SPR spectroscopy using a T200 device from Biacore (GE Healthcare). The standard conditions are 25° C. and a flow rate of 30 µl/min. Different lyophilizates of the D peptides were placed in the 1×PBS running buffer and serially diluted. The method used was a "single-cycle" kinetics method, wherein five increasing analyte concentrations were pumped over the immobilized flow cells. The contact times selected, depending on the analyte, were 90 to 120 s for association and dissociation and 1800 to 5400 s for the final dissociation. The sensorgrams were double referenced with the aid of an unloaded flow cell and the running buffer that was used. The binding curves were evaluated by way of kinetic fit models (heterogeneous binding model) using the Biacore T200 evaluation software (version 2.0).

Figure 6:
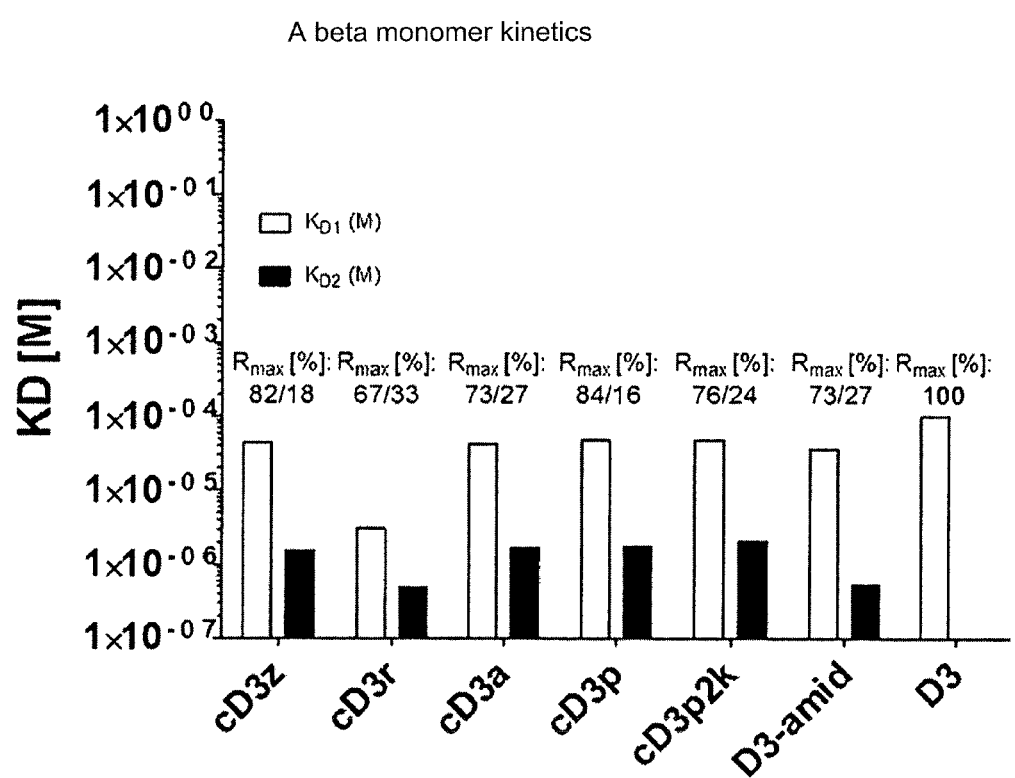
FIG. 6: $K_D$ values (kinetics) for amyloid beta monomer.
Figure 7:
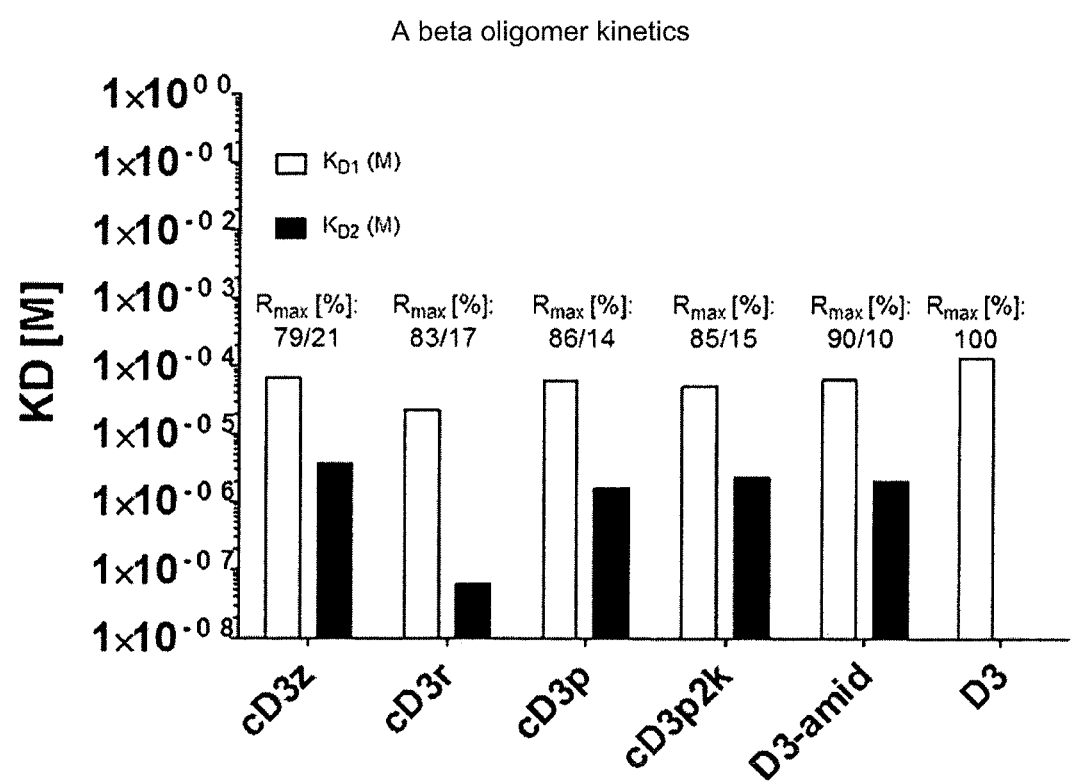
FIG. 7: $K_D$ values (kinetics) for amyloid beta oligomer.
Figure 8:
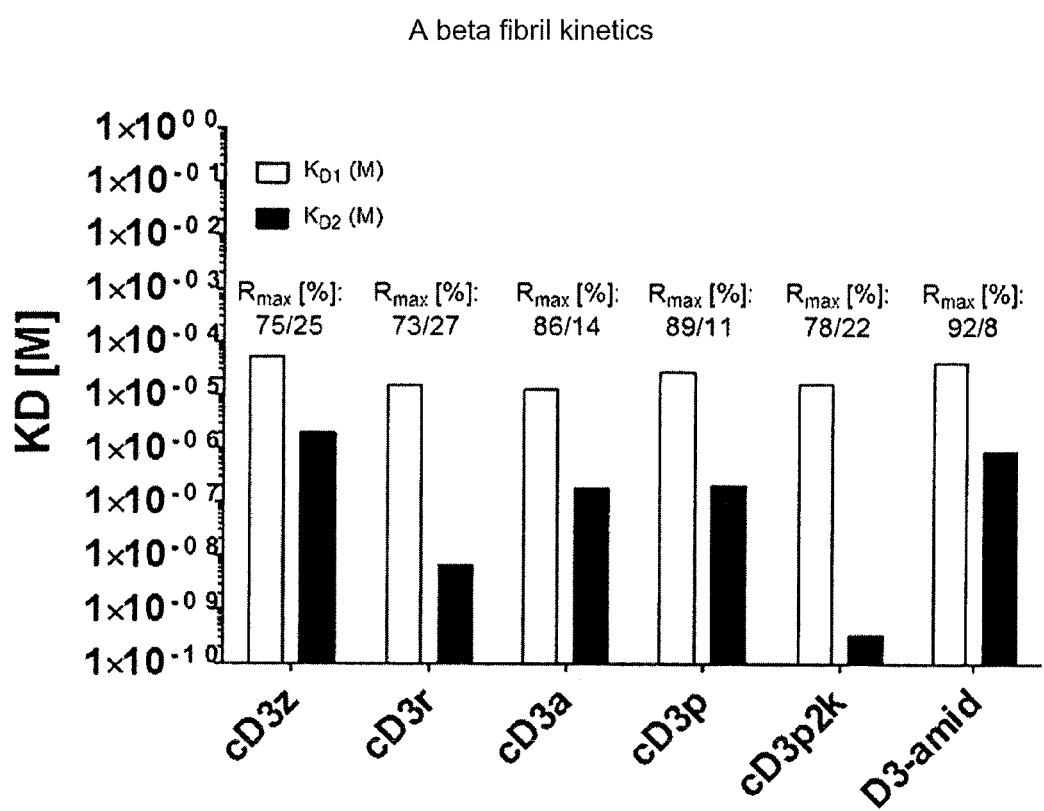
FIG. 8: $K_D$ values (kinetics) for amyloid beta fibrils.

FIGS. 6 to 8 show the results of the binding behavior of the peptides according to the invention (affinity study). The figures show data for the kinetic evaluation of the binding strength of the various candidates to amyloid beta monomers (FIG. 6), amyloid beta oligomers (FIG. 7), and amyloid beta fibrils (FIG. 8). The two binding constants that result when fitting a heterogeneous binding model are shown in each case, plotted as white bars and black bars. It is important to remember that a logarithmic scale is shown here, which means that minor differences in the bar size represent major differences in the dissociation constant $K_D$. White bars are the respective low-affinity sites and the binding strengths thereof, and black bars show the high-affinity binding sites and the binding strengths thereof.

It is shown that a homogeneous 1:1 binding model is only sufficient for fitting the binding curves in the case of the linear peptide D3, in which the free C-terminus has a negative charge.

It is also shown that the white bars for the low-affinity binding sites are similarly high in almost all instances of the cyclized peptides that are used. However, big differences result in the high-affinity binding sites, which are shown as black bars.

It also becomes apparent that the cyclic cD3r (SEQ ID NO. 9) does very well among the monomers (FIG. 6), which is to say has particularly high affinity.

Among the oligomers that are of particular interest, cD3r binds even more strongly by two orders of magnitude than the other cyclized peptides according to the invention (FIG. 7).

The cD3r also does very well among the fibrils compared to the other peptides according to the invention, wherein here, as a peculiarity, the peptide according to the invention cD3(P2K) (SEQ ID NO. 12) does extremely well and advances as far as the sub-pM binding range (FIG. 8).

It is also shown that the amidated form of the D3 binds more strongly to amyloid beta monomer and amyloid beta oligomer than the non-amidated form of the D3. This is evident from the lower $K_{D1}$ value for the low-affinity site and the presence of a high-affinity site, which has a $K_{D2}$ in the sub-µ range.

The $R_{max}$ values in FIGS. 6 to 8 indicate how strong the contribution of the respective $K_D$ to the overall loading capacity is. In the example of the oligomers (FIG. 7), an $R_{max}$ of 79/21% is shown for the peptide cD3z. cD3z denotes the cD3 zero, which is to say cyclized D3 without any further amino acid attachments. The white bar indicates that the low-affinity site can yield a total of 79% of the RU total loading strength and $K_{D2}$ a total of 21% of the RU. This means that a ratio of approximately 1:4 exists for this peptide at binding sites, which is to say there are approximately 4 times as many low-affinity sites as high-affinity sites.

Such differences between the low-affinity site and the high-affinity site occur with the peptides according to the invention.

The observation that no high-affinity site is yielded for the linear peptide D3 when fitting the experimental binding data can be explained by the fact that it either does not bind to the high-affinity site, or that the affinities to the high-affinity site and low-affinity site cannot be distinguished.

It becomes apparent from this data that the linear D3 binds only a low-affinity site, but not a high-affinity site in the case of amyloid beta oligomer.

TABLE 2

| Experiment number | Peptide | Mouse model | Dose | Water maze | Object recognition | Plaque pathology | SHIRPA | Rotarod |
|---|---|---|---|---|---|---|---|---|
| 1 | D3 amidated | TBA | 0.1 mg/day | not carried out | not carried out | not carried out | | significant (FIG. 2) |
| 2 | D3D3 amidated | TgSwDI | 1 mg/4 weeks | significant day 5 | significant (FIG. 1) | significant | not carried out | not carried out |
| 3 | D3D3 amidated | TBA | 0.1 mg/day | not carried out | not carried out | not carried out | significant (FIG. 3) | significant (FIG. 2) |
| 4 | RD2D3 amidated | TgSwDI | 7 mg/4 weeks | significant day 5 (FIG. 4) | significant (FIG. 5) | | not carried out | not carried out |

Each of the substance was administered i.p. for 4 weeks (micropump).

---

The invention claimed is:

1. A peptide comprising an amino acid sequence which binds to amyloid beta species,
   wherein the peptide has been modified by cyclization,
   wherein the amino acid sequence is selected from the group consisting of SEQ ID NO: 1, SEQ ID NO: 9, SEQ ID NO: 10, SEQ ID NO: 11 and homologs thereof, with an identity of at least 80%, and
   wherein the peptide's binding affinity to the amyloid beta species is increased as compared to an analogous peptide without any modification.

2. The peptide according to claim 1, wherein D-enantiomeric amino acids make up at least 50% of the amino acid sequence.

3. The peptide according to claim 1, being linked to a further substance.

4. The peptide according to claim 1, comprising at least two amino acid sequences, one of which is SEQ ID NO: 1 and the other being selected from the group consisting of SEQ ID NO: 2, SEQ ID NO: 3, SEQ ID NO: 9, SEQ ID NO: 10, SEQ ID NO: 11, SEQ ID NO: 12 and homologs thereof.

5. The peptide according to claim 4, wherein the at least two amino acid sequences together form a second amino acid sequence selected from the group consisting of SEQ ID NO: 4 and SEQ ID NO: 5, and homologs thereof.

6. A method for producing a peptide according to claim 1, comprising a step of producing the peptide by way of peptide synthesis or mutagenesis.

7. A kit comprising a peptide according to claim 1.

8. A composition comprising a peptide according to claim 1.

* * * * *

SEQUENCE LISTING

<160> NUMBER OF SEQ ID NOS: 12

<210> SEQ ID NO 1
<211> LENGTH: 12
<212> TYPE: PRT
<213> ORGANISM: Artificial Sequence
<220> FEATURE:
<223> OTHER INFORMATION: D-Peptide, RD2

<400> SEQUENCE: 1

Pro Thr Leu His Thr His Asn Arg Arg Arg Arg Arg
1               5                   10

<210> SEQ ID NO 2
<211> LENGTH: 12
<212> TYPE: PRT
<213> ORGANISM: Artificial Sequence
<220> FEATURE:
<223> OTHER INFORMATION: D-Peptide, D3

<400> SEQUENCE: 2

Arg Pro Arg Thr Arg Leu His Thr His Arg Asn Arg
1               5                   10

<210> SEQ ID NO 3
<211> LENGTH: 12
<212> TYPE: PRT
<213> ORGANISM: Artificial Sequence
<220> FEATURE:
<223> OTHER INFORMATION: D-Peptide, DB3

<400> SEQUENCE: 3

Arg Pro Ile Thr Arg Leu Arg Thr His Gln Asn Arg
1               5                   10

<210> SEQ ID NO 4
<211> LENGTH: 24
<212> TYPE: PRT
<213> ORGANISM: Artificial Sequence
<220> FEATURE:
<223> OTHER INFORMATION: D-Peptide, RD2D3

<400> SEQUENCE: 4

Pro Thr Leu His Thr His Asn Arg Arg Arg Arg Arg Pro Arg Thr
1               5                   10                  15

Arg Leu His Thr His Arg Asn Arg
            20

<210> SEQ ID NO 5
<211> LENGTH: 24

```
<212> TYPE: PRT
<213> ORGANISM: Artificial Sequence
<220> FEATURE:
<223> OTHER INFORMATION: D-Peptide, D3RD2

<400> SEQUENCE: 5

Arg Pro Arg Thr Arg Leu His Thr His Arg Asn Arg Pro Thr Leu His
1               5                   10                  15

Thr His Asn Arg Arg Arg Arg Arg
            20

<210> SEQ ID NO 6
<211> LENGTH: 24
<212> TYPE: PRT
<213> ORGANISM: Artificial Sequence
<220> FEATURE:
<223> OTHER INFORMATION: D-Peptide, D3D3

<400> SEQUENCE: 6

Arg Pro Arg Thr Arg Leu His Thr His Arg Asn Arg Arg Pro Arg Thr
1               5                   10                  15

Arg Leu His Thr His Arg Asn Arg
            20

<210> SEQ ID NO 7
<211> LENGTH: 24
<212> TYPE: PRT
<213> ORGANISM: Artificial Sequence
<220> FEATURE:
<223> OTHER INFORMATION: D-Peptide, RD2RD2

<400> SEQUENCE: 7

Pro Thr Leu His Thr His Asn Arg Arg Arg Arg Arg Pro Thr Leu His
1               5                   10                  15

Thr His Asn Arg Arg Arg Arg Arg
            20

<210> SEQ ID NO 8
<211> LENGTH: 24
<212> TYPE: PRT
<213> ORGANISM: Artificial Sequence
<220> FEATURE:
<223> OTHER INFORMATION: D-Peptide, DB3DB3

<400> SEQUENCE: 8

Arg Pro Ile Thr Arg Leu Arg Thr His Gln Asn Arg Arg Pro Ile Thr
1               5                   10                  15

Arg Leu Arg Thr His Gln Asn Arg
            20

<210> SEQ ID NO 9
<211> LENGTH: 13
<212> TYPE: PRT
<213> ORGANISM: Artificial Sequence
<220> FEATURE:
<223> OTHER INFORMATION: D-Peptide, D3r

<400> SEQUENCE: 9

Arg Pro Arg Thr Arg Leu His Thr His Arg Asn Arg Arg
1               5                   10

<210> SEQ ID NO 10
<211> LENGTH: 13
<212> TYPE: PRT
<213> ORGANISM: Artificial Sequence
```

```
<220> FEATURE:
<223> OTHER INFORMATION: D-Peptide, D3p

<400> SEQUENCE: 10

Arg Pro Arg Thr Arg Leu His Thr His Arg Asn Arg Pro
1               5                   10

<210> SEQ ID NO 11
<211> LENGTH: 13
<212> TYPE: PRT
<213> ORGANISM: Artificial Sequence
<220> FEATURE:
<223> OTHER INFORMATION: D-Peptide, D3a

<400> SEQUENCE: 11

Arg Pro Arg Thr Arg Leu His Thr His Arg Asn Arg Ala
1               5                   10

<210> SEQ ID NO 12
<211> LENGTH: 12
<212> TYPE: PRT
<213> ORGANISM: Artificial Sequence
<220> FEATURE:
<223> OTHER INFORMATION: D-Peptide, D3(p2k)

<400> SEQUENCE: 12

Arg Lys Arg Thr Arg Leu His Thr His Arg Asn Arg
1               5                   10
```